United States Patent [19]

Chibata et al.

[11] Patent Number: 4,486,532
[45] Date of Patent: * Dec. 4, 1984

[54] PROCESS FOR PREPARING L-MALIC ACID

[75] Inventors: Ichiro Chibata, Suita; Tetsuya Tosa, Kyoto; Tadashi Sato; Kozo Yamamoto, both of Takatsuki, all of Japan

[73] Assignee: Tnanbe Seiyaku Co., Ltd., Osaka, Japan

[*] Notice: The portion of the term of this patent subsequent to Nov. 25, 1992 has been disclaimed.

[21] Appl. No.: 700,999

[22] Filed: Jun. 29, 1976

[30] Foreign Application Priority Data

Jul. 11, 1975 [JP] Japan ................... 50-85672

[51] Int. Cl.$^3$ ............................. C12P 7/46
[52] U.S. Cl. ......................... 435/145; 435/180; 435/182; 435/840; 435/843; 435/849; 435/873; 435/938
[58] Field of Search ............ 195/29, 30, 36 R, 37, 195/47, 66 R, 114, 63, 68; 435/145, 180, 182, 840, 843, 849, 873, 938

[56] References Cited

U.S. PATENT DOCUMENTS

| | | | |
|---|---|---|---|
| 2,972,566 | 2/1961 | Kitahara | 195/30 |
| 3,063,910 | 11/1962 | Abe et al. | 195/36 R |
| 3,922,195 | 11/1975 | Chibata et al. | 195/30 |
| 3,980,520 | 9/1976 | Degen et al. | 195/30 |

FOREIGN PATENT DOCUMENTS 69289  6/1975  Japan.

OTHER PUBLICATIONS

Dixon et al, "Enzymes" Academic Press 1964, pp. 32–35, 387–389, 548–549 and 634–635.
Rose et al, "The Condensed Chemical Dictionary", Van Nostrand Reinhold Co. 1970, p. 118.

Primary Examiner—R. B. Penland
Attorney, Agent, or Firm—Jordan B. Bierman

[57] ABSTRACT

At least one acryl or allyl monomer is polymerized in an aqueous suspension containing a fumarase-producing microorganism. The resultant immobilized fumarase-producing microorganism is contacted with bile acids or salts thereof. Then, the immobilized fumarase-producing microorganism is subjected to enzymatic reaction with fumaric acid or a salt thereof. L-Malic acid is prepared without the production of the by-product succinic acid.

23 Claims, No Drawings

PROCESS FOR PREPARING L-MALIC ACID

This invention relates to a process for preparing L-malic acid from fumaric acid.

Various methods for preparing L-malic acid are known. For example, L-malic acid is prepared by cultivating a fumarase-producing microorganism (i.e., a microorganism having the ability to convert fumaric acid into L-malic acid) in a nutrient medium containing fumaric acid or a salt thereof, and recovering L-malic acid from the resultant fermentation broth. It is also prepared by contacting microbial cells of a fumarase-producing microorganism with fumaric acid or a salt thereof. However, these methods are disadvantageous for the large scale production of L-malic acid. L-malic acid prepared according to these known methods is contaminated with microbial cells, nutrient sources and/or proteins. Accordingly, additional steps of removing the microbial cells and other contaminants from the product are required to recover highly pure L-malic acid. Moreover, when the enzymatic reaction is completed, the reaction solution is boiled and/or acidified to destroy the fumarase-producing microorganism, and precipitates of the microorganism are filtered off. Thus, the fumarase-producing microorganism can be used only once and must be discarded thereafter.

Recently, Chibata et al disclosed that a fumarase-producing microorganism immobilized with an acrylamide polymer can be used for production of L-malic acid [Japanese Patent Application No. 118832/1973 (laid open to the public without examination on June 10, 1975 under No. 69289/1975)]. This method comprises the steps of polymerizing acrylamide monomers in an aqueous suspension containing a fumarase-producing microorganism to produce an immobilized fumarase-producing microorganism, and subjecting the immobilied fumarase-producing microorganism to enzymatic reaction with fumaric acid. This method is still disadvantageous in that the L-malic acid produced is inevitably contaminated with by-products such as succinic acid. Further, once L-malic acid is contaminated with succinic acid, it is quite difficult to remove the latter by ordinary purification procedures.

We have now found that the fumarase activity of an immobilized fumarase-producing microorganism can be enhanced remarkably by contacting the immobilized fumarase-producing microorganism with bile acids or salts thereof. We have also found that the immobilized fumarase-producing microorganism, treated with bile acids, does not produce substantial amounts of by-products such as succinic acid by enzymatic reaction thereof with fumaric acid.

One object of the present invention is to provide an immobilized microorganism which affords high activity of fumarase for a long period of time. Another object of the present invention is to provide an immobilized fumarase-producing microorganism which, when contacted with fumaric acid, does not produce substantial amounts of by-products such as succinic acid. Another object of this invention is to provide an improved method of preparing L-malic acid from fumaric acid. Further objects of the present invention will be apparent from the descriptions which follow.

According to the present invention, L-malic acid can be prepared by the steps of polymerizing at least one acryl or allyl monomer in an aqueous suspension containing a fumarase-producing microorganism to produce an immobilized fumarase-producing microorganism, contacting the immobilized fumarase-producing microorganism with at least one member of the group consisting of bile acids or salts thereof, and then subjecting the immobilized fumarase-producing microorganism to enzymatic reaction with fumaric acid or a salt thereof.

Preferred examples of the fumarase-producing microorganisms which are employed in the present invention include *Brevibacterium ammoniagenes* IAM (Institute of Applied Microbiology, Tokyo University, Japan) 1641 (ATCC 6871) [of. Bergey's Manual of Determinative Bacteriology, 7th edition, p. 499 (1957)], *Brevibacterium ammoniagenes* IAM 1645 (ATCC 6872) [of. ibid., p. 499], *Corynebacterium equi* IAM 1038]of. ibid., p. 588], *Escherichia coli* ATCC 11303 [of. ibid, p. 336], *Microbacterium flavum* IAM 1642 [of. ibid., p. 601], *Proteus vulgaris* IFO (Institute for Fermentation, Osaka, Japan) 3045 [of. ibid, p. 365], *Pichia farinosa* IFO 0574 [of. The Chemistry and Biology of Yeast (edited by A. H. Cook), p. 37 (1958)]. All of these microorganisms are publicly available from the above-mentioned depositories. In this connection, however, it should be noted that the present invention is not limited to the use of these specific microorganisms, but includes within its scope the use of all furmarase-producing microorganisms such as those belonging to the genera of Brevibacterium, Corynebacterium, Escherichia, Microbacterium, Proteus and Pichia. Suitable amounts of the fumarase-producing microorganism which are employed in the present invention are in the range of 0.1 to 5 g, especially 1 to 3 g per g of the acryl or allyl monomers used. The polymerizaton reaction of the present invention serves to tightly entrap the microorganisms into the lattice of the polymer.

The polymerization reaction of the present invention can be carried out in the presence of a polymerization initiator and a polymerization accelerator. Potassium persulfate, ammonium persulfate, vitamin $B_2$, Methylene Blue, etc. are suitable as the polymerization initiator. On the other hand, $\beta$-(dimethylamino)-propionitrile, N,N,N',N'-tetramethyl-ethylenediamine, etc. are employed as the polymerization accelerator. Suitable amounts of the polymerization initiator which are added to the aqueous suspension of the fumarase-producing microorganism are in the range of 1 to 100 mg per g of the acryl or allyl monomers. Suitable amounts of the polymerization accelerator are in the range of 10 to 200 mg per g of the acryl or allyl monomers. It is preferred to carry out the reaction at a temperature of between about 0° and 50° C., especially between about 10° and 30° C. The reaction may be completed within 5 to 60 minutes. The acryl or allyl monomers which are suitable for use in the present invention include acrylic acid, methacrylic acid, acrylamide, hydroxy-lower alkyl methacrylate, N,N'-lower alkylene-bis (acrylamide), bis(acrylamidomethyl) ether, N,N'-diacryl-ethyleneurea, lower alkylene glycol dimethacrylate, N,N',N''-triacryl-hexahydrotriazine,diallyl maleate, N,N'-diallyl-tartaric acid diamide and triallyl cyanurate. 2-Hydroxyethyl methacrylate and 3-hydroxypropyl methacrylate are preferably employed as the hydroxy-lower alkyl methacrylate, N,N'-methylene-bis(acrylamide) and N,N'-propylene-bis(acrylamide) are suitable as the N,N'-lower alkylene-bis (acrylamide). Preferred examples of the lower alkylene glycol dimethacrylate include ethylene glycol dimethacrylate and 1,3-butylene glycol dimethacrylate. For the purpose of the present invention, it is suitable to entrap the fumarase-producing microorganism with a polymer obtained from one or two monomers mentioned above, particularly with a homopolymer of N,N'-lower alkylene-bis (acrylamide), bis(acrylamidomethyl) ether,N,N'-diacrylethyleneurea, lower alkylene glycol dimethacrylate,N,N'N"-triacryl-hexahydrotriazine, N,N'-diallyl-tartaric acid diamide or triallyl cyanurate; or a copolymer of acrylamide or hydroxy-lower alkyl methacrylate and a monomer selected from the group consisting of N,N'-lower alkylene-bis(acrylamide), bis-(acrylamidomethyl)ether, N,N'-diacryl-ethyleneurea, lower alkylene glycol dimethacrylate, N,N',N"-triacryl-hexahydrotriazine, diallyl maleate, N,N'-diallyl-tartaric acid diamide and triallyl cyanurate. Suitable amounts of N,N'-lower alkylene-bis(acrylamide), bis(acrylamidomethyl)ether, N,N'-diacryl-ethyleneurea, lower alkylene glycol dimethacrylate, N,N',N"-triacryl-hexahydrotriazine, diallyl maleate, N,N'-diallyl-tartaric acid diamide or triallyl cyanurate, which are used to copolymerize with acrylamide or hydroxy-lower alkyl methacrylate, are 10 to 200 mg, especially 50 to 100 mg, per g of acrylamide or hydroxy-lower alkyl methacrylate. After the polymerization reaction is completed as above, the resultant gel is granulated by passing it through a sieve to form granules having a diameter of between about 0.5 mm and 30 mm especially between about 1 and 5 mm.

The immobilized fumarase-producing microorganism thus obtained is then contacted with at least one of bile acids or salts thereof. This treatment can be easily carried out by soaking or immersing the immobilized preparation in an aqueous solution of bile acids or salts thereof. A preferred concentration of bile acids or salts thereof in the aqueous solution is between about 0.1 and 5 w/v %, especially between about 0.2 and 2 w/v %. It is preferred to carry out the treatment at a temperature of between about 0° and 50° C. especially between about 20° and 40° C., and at a pH of between about 5 and 10, and especially between about 6 and 8. It is also preferred to carry out the treatment for about 2 to 24 hours. In carrying out the above-mentioned treatment, fumaric acid or a salt thereof may be added to the solution as a stabilizer. Various bile acids, either natural or synthetic, can be employed for the present invention. Examples of such acids include monohydroxycholanic acid (e.g., lithocholic acid, 6-hydroxycholanic acid, 7-hydroxycholanic acid, 11-hydroxycholanic acid, 12-hydroxycholanic acid), dihydroxycholanic acid (e.g., hyodesoxycholic acid, desoxycholic acid, isodesoxycholic acid, chenodesoxycholic acid, ursodesoxycholic acid, lagodesoxycholic acid, 3,11-dihydroxycholanic acid, 11-12-dihydroxycholanic acid), trihydroxycholanic acid (e.g., cholic acid, 3,11,12-trihydroxycholanic acid), taurocholic acid, glycocholic acid, taurodesoxycholic acid, glycodesoxycholic acid, 3-hydroxy-6-ketocholanic acid, 3-hydroxy-6-ketoallo-cholanic acid and a mixture of these acids. These bile acids may be used either in the form of free bases or salts thereof such as alkali metal (e.g., sodium and potassium) and alkaline earth metal (e.g. magnesium) salts. Further, in the present invention it is not always necessary to use pure crystals of the bile acids and the salts thereof. For example, ox bile extract which is commercially available on the market may be employed without purification. Ox bile extract is mainly composed of the sodium salts of taurocholic and glycocholic acids. As mentioned hereinbefore, the fumarase activity of the immobilized preparation is enhanced remarkably by contacting it with these bile acids. For example, the immobilized fumarase-producing microorganism treated with at least one of the bile acids and salts thereof shows an enzymatic activity at least 15 times greater than that of the non-treated one. Furthermore, the immobilized fumarase-producing microorganism treated as above, when contacted with fumaric acid or a salt thereof, does not substantially produce succinic acid.

After the above-mentioned treatment, the immobilized furmarase-producing mircroorganism is contacted with fumaric acid or a salt thereof. Suitable examples of the salt of fumaric aicd which is used in the present invention include alkali metal (e.g., sodium, potassium) salts, alkaline earth metal (e.g., calcium, barium) salts and ammonium salts. The enzymatic reaction can be carried out at a temperature of between about 5° and 60° C., especially between about 10° and 50° C. It is preferred to carry out the reaction at a pH of between about 5 and 10, especially between about 6 and 8. The concentration of the substrate (i.e., fumaric acid or a salt thereof) is not critical in the present invention. For example, fumaric acid or a salt thereof is dissolved or suspended in water at any concentration. The immobilized fumarase-producing microorganism is added to the aqueous fumarate solution or suspension and the mixture is stirred. L-malic acid is produced in the reaction mixture. The optimum conditions for conversion of fumaric acid or a salt thereof to L-malic acid can be readily obtained by adjusting the reaction time.

Alternatively, the enzymatic reaction of the present invention can be performed by a column method. The column method enables the reaction to be carried out continuously. For example, the immobilized microorganism is charged into a column, and an aqueous solution containing an alkali metal salt of fumaric acid or ammonium fumarate is passed through the column. An aqueous solution containing the corresponding L-malate is obtained as the effluent. On the other hand, when a mixture of sodium fumarate and calcium fumarate is employed as the substrate an aqueous suspension of the substrate is filtered, and the filtrate is passed through the column of the immobilized fumarase-producing microorganism. The effluent thus obtained is mixed with the aqueous suspension of the substrate. The mixture is again filtered. and the filtrate is passed through the column. Such operations are repeated continuously, whereby calcium fumarate can be almost entirely converted to calcium L-malate.

Recovery of L-malic acid from the reaction mixture or effluent can be carried out in a conventional manner. When the alkali metal salt of fumaric acid is employed as the substrate, for example, L-malic acid can be recovered by acidifying the reaction mixture or effluent with hydrochloric acid, filtering it to remove the precipitates of fumaric acid, adding calcium carbonate or calcium hydroxde to the filtrate to precipitate calcium L-malate and then neutralizing the calcium L-malate with sulfuric acid.

In carrying out the enzymatic reaction, the conversion rate (%) of fumaric acid or a salt thereof to L-malic acid depends mainly upon the enzymatic potency of the immobilized microorganism, the temperature or the reaction time. In the case of the column method, however, the optimum reaction conditions for conversion of furamic acid or a salt thereof to L-malic acid can be readily obtained by adjusting the flow rate of the substrate solution In any case, the immobilized microorganism treated with bile acid or salts thereof retains a high level of enzymatic activity during the reaction. Moreover, due to sufficient durability of the enzymatic activity thereof, the immobilized microorganism of the present invention can be used repeatedly for the enzymatic reaction.

Practical and presently-preferred embodiments of the present invention are illustratively shown in the following Examples. In this specification, the term "lower alkyl" refers to an alkyl group having one to four carbon atoms. The term "lower alkylene" refers to an alkylene group having one to four carbon atoms. In the following Examples, the amount of L-malic acid produced was assayed in accordance with the method described in "Analytical Chemistry, 29, 283 (1957)". The amount of succinic acid was assayed by paper chromatography using a mixture of n-butanol, acetic acid and water (4:1:1) as the solvent and 0.1% Bromphenol Blue as a coloring reagent.

EXAMPLE 1

(1) An aqueous nutrient medium(pH 7.0) containing the following ingredients is prepared.

| | |
|---|---|
| Glucose | 2.0 w/v % |
| Fumaric acid | 0.5 w/v % |
| Urea | 0.2 w/v % |
| Monopotassium phosphate | 0.2 w/v % |
| Magnesium sulfate 7 H$_2$O | 0.05 w/v % |
| Corn steep liquor | 1.0 w/v % |

Each of the fumarase-producing microorganisms shown in Table 1 is inoculated into 100 ml of the medium. The medium is cultivated at 30° C. for 20 hours under shaking. Then, the microbial cells are collected by centrifugation. One g of the microbial cells is suspended in 4 ml of a physiological saline solution. 750 mg of acrylamide, 40mg of N,N'-methylene-bis(acrylamide), 0.5 ml of an aqueous 5 v/v % β-(dimethylamino)-propionitrile solution and 0.5 ml of an aqueous 1 w/v % potassium persulfate solution are added to the suspension. The mixture is allowed to stand at 25° C. for 10 minutes. The gel thus obtained is granulated by passing it through a sieve to form granules having a diameter of 2 mm. The granules are washed with a physiological saline solution. 7.5 g of an immobilized preparation of the fumarase-producing microorganism are obtained.

(2) 7.5 g of the immobilized preparation obtained in paragraph (1) are suspended in 30 ml of an aqueous 1 M sodium fumarate solution(pH 7.5) containing 3 mg/ml of ox bile extract (manufactured by Inolex Pharmaceutical Division Wilson Pharmaceutical & Chemical Corporation, Illinois, U.S.A.) or 2 mg/ml of desoxycholic acid. The suspension is allowed to stand at 37° C. for 20 hours. Then, the immobilized preparation is collected by filtration and washed with a physiological saline solution.

(3) 7.5 g of the immobilized preparation obtained in paragraph (1) or (2) are added to 30 ml of an aqueous 1 M sodium fumarate solution(pH 7.5). The mixture is stirred at 37° C. for one hour. Then, the amount of L-malic acid produced in the reaction mixture is estimated. The results are shown in Table 1.

TABLE 1

| | Amount of L-malic acid produced (μmoles/hr/g of cells) | | |
|---|---|---|---|
| | The immobilized preparation obtained in paragraph (1) | The immobilized preparation obtained in paragraph (2) Bile acids used | |
| Immobilized cells | | Ox bile extract | Desoxycholic acid |
| Brevibacterium ammoniagenes IAM 1641 | 178 | 2,700 | 2,650 |
| Brevibacterium ammoniagenes IAM 1645 | 490 | 7,800 | 7,430 |
| Corynebacterium equi IAM 1038 | 85 | 3,800 | 3,050 |
| Microbacterium flavum IAM 1642 | 195 | 3,300 | 3,420 |
| Proteus vulgaris IFO 3045 | 161 | 2,180 | 2,200 |

(4) 7.5 g of the immobilized preparation obtained in paragraph (1) or (2) are added to 30 ml of an aqueous 1 M sodium fumarate solution(pH 7.5). The mixture is stirred at 37° C. for 24 hours. Then, the amount of each of L-malic acid and succinic acid in the reaction mixture is estimated and the quantitative ratio of succinic acid to L-malic acid is calculated therefrom. The results are shown in Table 2.

TABLE 2

| | Quantitative ratio of succinic acid to L-malic acid (%) | |
|---|---|---|
| Immobilized cells | The immobilized preparation obtained in paragraph (1) | The immobilized preparation obtained in paragraph (2) Bile acid used Ox bile extract |
| Brevibacterium ammoniagenes IAM 1641 | >2.5 | <0.5 |
| Brevibacterium ammoniagenes IAM 1645 | >2.5 | <0.5 |
| Corynebacterium equi IAM 1038 | >2.5 | <0.5 |
| Microbacterium flavum IAM 1642 | >5.0 | <0.5 |
| Proteus vulgaris IFO 3045 | 1-2.5 | <0.5 |

EXAMPLE 2

30 g of the immobilized preparation of *Brevibacterium ammoniagenes* IAM 1645, obtained in the same manner as described in Example 1-(1), are suspended in 100 ml of an aqueous 1 M sodium fumarate solution (pH 7.5) containing 3 mg/ml of ox bile extract (manufactured by Inolex Pharmaceutical Division Wilson Pharmaceutical & Chemical Corporation, Illinois, U.S.A.). The suspension is allowed to stand at 37° C. for 20 hours, and is then filtered. The immobilized preparation thus obtained is washed with a physiological saline solution and charged into a column (2.2 cm × 19.5 cm). One liter of an aqueous 1 M sodium fumarate solution(pH 7.5) is passed through the column at 37° C. at a flow rate of 20 ml/hr. The effluent is acidified with 200 ml of concentrated hydrochloric acid, and then filtered to remove the precipitates of fumaric acid. The filtrate is adjusted to pH 6.0 with about 70 g of calcium hydroxide. The crystalline precipitates are collected by filtration, washed with water and then dried. 150 g of calcium L-malate dihydrate are thereby obtained. 350 ml of 2N-sulfuric acid are added to calcium L-malate dihydrate. The mixture is filtered to remove the precipitates. The filtrate is passed through a column charged with about 150 ml of Amberlite IR-120(H+ type) and then passed through a column charged with about 150 ml of Amberlite IR-45 (OH− type). The effluent is concentrated at 60° C. under reduced pressure. The crystalline precipitates are collected by filtration, washed with a small amount of acetone and then dried. 50 g of L-malic acid are thereby obtained. The mother liquor is concentrated and the concentrated solution is treated in the same manner as above. 22 g of L-malic acid are thereby obtained. Total amount 77 g M. P. 100° C. $[\alpha]_D^{20} = -2.2°(C=8.5, H_2O)$

EXAMPLE 3

20 g of the immobilized preparation of *Brevibacterium ammoniagenes* IAM 1645, prepared in the same manner as described in Example 1-(1), are suspended in 90 ml of an aqueous 1 M sodium fumarate solution (pH 7.5) containing 3 mg/ml of ox bile extract (manufactured by Inolex Pharmaceutical Division Wilson Pharmaceutical & Chemical Corporation, Illinois, U.S.A.). The suspension is allowed to stand at 37° C. for 20 hours, and is then filtered. The immobilized preparation thus obtained is washed with a physiological saline solution and then charged into a column (1.6 cm×15 cm). An aqueous 1 M sodium fumarate solution (pH 7.5) is passed through the column at a flow rate of 6 ml/hr or 25 ml/hr. The L-malic acid content in the effluent is estimated and the percent conversion of fumaric acid to L-malic acid is calculated therefrom. The results are shown in Table 3.

TABLE 3

| Operation time (days) | Conversion rate of fumaric acid L-malic acid (%) Flow rate | |
|---|---|---|
| | 6 ml/hr | 25 ml/hr |
| 1 | 82 | 54 |
| 4 | 82 | 53 |
| 6 | 82 | 50 |
| 8 | 82 | 50 |
| 11 | 82 | 49 |
| 15 | 82 | 47 |
| 18 | 82 | 46 |
| 22 | 82 | 42 |
| 26 | 82 | 40 |
| 28 | 82 | 39 |

EXAMPLE 4

30 g of the immobilized preparation of *Microbacterium flavum* IAM 1642, prepared in the same manner as described in Example 1-(1), are suspended in 100 ml of an aqueous 1 M sodium fumarate solution (pH 7.5) containing 3 mg/ml of ox bile extract (manufactured by Inolex Pharmaceutical Division Wilson Pharmaceutical & Chemical Corporation, Illinois, U.S.A. ). The suspension is allowed to stand at 37° C. for 20 hours, and is then filtered. The immobilized preparation thus obtained is suspended in 500 ml of an aqueous 1 M sodium fumarate solution (pH 7.5). The suspension is stirred at 37° C. for a period of time. The L-malic acid content in the reaction mixture is estimated and the percent conversion of fumaric acid to L-malic acid is calculated therefrom. The results are shown in Table 4.

TABLE 4

| Operation time (hours) | Conversion rate of fumaric acid to L-malic acid (%) |
|---|---|
| 3 | 14 |
| 6 | 25 |
| 9 | 38 |
| 16 | 78 |
| 24 | 82 |
| 30 | 82 |

EXAMPLE 5

30 g of the immobilized preparation of *Brevibacterium ammoniagenes* IAM 1645, prepared in the same manner as described in Example 1-(1), are suspended in 120 ml of an aqueous 1 M sodium fumarate solution (pH 7.5) containing 3 mg/ml of ox bile extract (manufactured by Inolex Pharmaceutical Division Wilson Pharmaceutical & Chemical Corporation, Illinois, U.S.A.). The suspension is allowed to stand at 37° C. for 20 hours, and is then filtered. The immobilized preparation thus obtained is washed with a physiological saline solution and then charged into a column (1.72 cm×28 cm). On the other hand, a substrate suspension is prepared by adding 500 ml of an aqueous 1 M calcium fumarate suspension (pH 7.5) to 150 ml of an aqueous 1 M sodium fumarate solution (pH 7.5). This substrate suspension is filtered under stirring and the filtrate is passed through the column at 37° C. at a flow rate of 200 ml/hr. The effluent is mixed with the substrate suspension. The mixture is again filtered under stirring and the filtrate is passed through the column. Such operations are continuously repeated for 40 hours. Then, the precipitates are collected by filtration, whereby 92 g of calcium L-malate dihydrate are obtained.

EXAMPLE 6

(1) *Corynebacterium equi* IAM 1038 is inoculated into 50 ml of an aqueous medium (pH 7.0) containing the same ingredients as described in Example 1-(1). The medium is cultivated at 30° C. for 20 hours under shaking. Then, the microbial cells are collected by centrifugation of the broth, and then suspended in 4 ml of a physiological saline solution. 750 mg of acrylamide, 40 mg of diallyl maleate, 0.5 ml of an aqueous 5 v/v % β-(dimethylamino)-propionitrile solution and 0.5 ml of an aqueous 1 w/v % potassium persulfate solution are added to the suspension. Then, the mixture is allowed to stand at 25° C. for 10 minutes. The gel thus obtained is granulated by passing it through a sieve to form granules having a diameter of 2 mm. The granules are washed with a physiological saline solution. 8 g of an immobilized preparation of *Corynebacterium equi* IAM 1038 are obtained.

(2) 8 g of the immobilized preparation obtained in paragraph (1) are suspended in 30 ml of an aqueous 1 M sodium fumarate solution (pH 7.5) containing 3 mg/ml of ox bile extract (manufactured by Inolex Pharmaceutical Division Wilson Pharmaceutical & Chemical Corporation, Illinois, U.S.A.). The suspension is allowed to stand 37° C. for 20 hours, and is then filtered. The immobilized preparation is washed with a physiological saline solution and then suspended in 50 ml of an aqueous 1 M sodium fumarate solution (pH 7.5). The mixture is stirred at 37° C. for a period of time. The reaction mixture is filtered to remove the immobilized preparation. The L-malic acid content in the filtrate is estimated and the percent conversion of fumaric acid to L-malic acid is calculated therefrom. The results are shown in Table 5.

TABLE 5

| Operation time (hours) | Conversion rate of fumaric acid to L-malic acid (%) |
| --- | --- |
| 2 | 20 |
| 4 | 35 |
| 6 | 50 |
| 16 | 80 |
| 24 | 82 |
| 30 | 82 |

EXAMPLE 7

30 g of the immobilized preparation of *Brevibacterium ammoniagenes* IAM 1645, prepared in the same manner as described in Example 1-(1), are suspended in 100 ml of 0.1 M sodium phosphate buffer (pH 7.5) containing 3 mg/ml of ox bile extract (manufactured by Inolex Pharmaceutical Division Wilson Pharmaceutical Division Wilson Pharmaceutical & Chemical Corporation, Illinois, U.S.A.). The suspension is allowed to stand at 37° C. for 20 hours, and is then filtered. The immobilized preparation thus obtained is washed with a physiological saline solution and then suspended in 500 ml of an aqueous 1 M sodium fumarate solution (pH 7.5). The suspension is stirred at 37° C. for a period of time. The reaction mixture is filtered to remove the immobilized preparation. The L-malic acid content in the filtrate is estimated and the percent conversation of fumaric acid to L-malic acid is calculated therefrom. The results are shown in Table 6.

TABLE 6

| Operation time (hours) | Conversion rate of fumaric acid to L-malic acid (%) |
| --- | --- |
| 2 | 20 |
| 4 | 38 |
| 6 | 50 |
| 8 | 62 |
| 16 | 78 |
| 24 | 82 |
| 30 | 82 |

EXAMPLE 8

(1) 4 g of the microbial cells of *Brevibacterium ammoniagenes* IAM 1645 are suspended in 16 ml of a physiological saline solution. 40 mg of bis(acrylamidomethyl)ether, 1.2 ml of an aqueous 0.112 w/v % N,N',N'-tetramethyl-ethylenediamine and 0.12 ml of an aqueous 2.5 w/v % ammonium persulfate are added to the suspension. The mixture is allowed to stand at 37° C. for 60 minutes. The gel thus obtained is granulated by passing it through a sieve to form granules having a diameter of 2 mm. The granules are washed with a physiological saline solution. 25 g of the immobilized preparation of *Brevibacterium ammoniagenes* IAM 1645 are obtained.

(2) 25 g of the immobilized preparation obtained in paragraph (1) are suspended in 120 ml of an aqueous 1 M sodium fumarate solution (pH 7.5) containing 3 mg/ml of ox bile extract (manufactured by Inolex Pharmaceutical Division Wilson Pharmaceutical & Chemical Corporation, Illinois, U.S.A.). The suspension is allowed to stand at 37° C. for 20, hours and is then filtered. The immobilized preparation thus obtained is washed with a physiological saline solution and suspended in 500 ml of an aqueous 1 M sodium fumarate solution (pH 7.5). The suspension is stirred at 37° C. for 24 hours. The reaction mixture is filtered to remove the immobilized preparation. The L-malic acid in the filtrate is recovered as calcium salt in the same manner as described in Example 2. 70 g of calcium L-malate dihydrate are obtained.

EXAMPLE 9

(1) 4 g of the microbial cells of *Brevibacterium ammoniagenes* IAM 1645 are suspended in 16 ml of a physiological saline solution. 40 mg of N,N'-diacryl-ethyleneurea, 1.2 ml of an aqueous 0.112 w/v % N,N,N',N'-tetramethyl-ethylenediamine and 0.12 ml of an aqueous 2.5 w/v % ammonium persulfate are added to the suspension. The mixture is allowed to stand at 37° C. for 60 minutes. The gel thus obtained is granulated by passing it through a sieve to form granules having a diameter of 2 mm. The granules are washed with a physiological saline solution. 25 g of the immobilized preparation of *Brevibacterium ammoniagenes* IAM 1645 are obtained.

(2) 25 g of the immobilized preparation obtained in paragraph (1) are suspended in 120 ml of an aqueous 1 M sodium fumarate solution (pH 7.5) containing 3 mg/ml of ox bile extract (manufactured by Inolex Pharmaceutical Division Wilson Pharmaceutical & Chemical Corporation, Illinois, U.S.A.). The suspension is allowed to stand at 37° C. for 20 hours, and is then filtered. The immobilized preparation thus obtained is washed with a physiological saline solution and suspended in 500 ml of an aqueous 1 M sodium fumarate solution (pH 7.5). The suspension is stirred at 37° C. for 24 hours. The reaction mixture is filtered to remove the immobilized preparation. The L-malic acid in the filtrate is recovered as calcium salt in the same manner as described in Example 2. 70 g of calcium L-malate dihydrate are obtained.

What we claim is:

1. A process for preparing L-malic acid which comprises the steps of polymerizing at least one acryl or allyl monomer in an aqueous suspension containing a fumarase-producing micro-organism to produce an immobilized fumarase-producing micro-organism, contacting the immobilized fumarase-producing microorganism with at least one member of the group consisting of bile acids or salts thereof, and then subjecting the immobilized fumarase-producing microorganism to enzymatic reaction with fumaric acid or a salt thereof.

2. The process according to claim 1, wherein the monomer is selected from the group consisting of acrylic acid, methacrylic acid, acrylamide, hydroxy-lower alkyl methacrylate, N,N'-lower alkylene-bis(acrylamide), bis(acrylamidomethyl)ether, N,N'-diacryl-ethyleneurea, lower alkylene glycol dimethacrylate, N,N',N''-triacryl-hexahydrotriazine, diallyl maleate, N,N'-diallyl-tartaric acid diamide and triallyl cyanurate.

3. A process for preparing L-malic acid which comprises the steps of polymerizing N,N'-lower alkylene-bis(acrylamide), bis(acrylamidomethyl)ether, N,N'-diacryl-ethyleneurea, lower alkylene glycol dimethacrylate, N,N',N''-triacryl-hexahydrotriazine, N,N'-diallyl-tartaric acid diamide or trially cyanurate, or copolymerizing acrylamide or hydroxy-lower alkyl methacrylate with N,N'-lower alkylene-bis(acrylamide), bis(acrylamidomethyl) ether, N,N'-diacryl-ethyleneurea, lower alkylene glycol dimethacrylate, N,N',N''-triacryl-hexahydrotriazine, diallyl maleate, N,N'-diallyl-tartaric acid diamide or triallyl cyanurate in an aqueous suspension of a fumarase-producing microorganism to produce an immobilized fumarase-producing microorganism, contacting the immobilized fumarase-producing microorganism with at least one member of the group consisting of bile acids or salts thereof, and then subjecting the immobilized fumarase-producing microorganism to enzymatic reaction with fumaric acid or a salt thereof.

4. A process for preparing L-malic acid which comprises the steps of polymerizing N,N'-lower alkylene-bis(acrylamide), bis(acrylamidomethyl)ether or N,N'-diacryl-ethyleneurea, or copolymerizing acrylamide with N,N'-lower alkylene-bis(acrylamide), bis(acrylamidomethyl)ether, N,N'-diacryl-ethyleneurea or diallyl maleate in an aqueous suspension of a fumarase-producing microorganism to produce an immobilized fumarase-producing microorganism, contacting the immobilized fumarase-producing microorganism with at least one member of the group consisting of bile acids or salts thereof, and then subjecting the immobilized fumarase-producing microorganism to enzymatic reaction with fumaric acid or a salt thereof.

5. The process according to claim 3, wherein the bile acids are selected from the group consisting of monohydroxycholanic acid, dihydroxycholanic acid, trihydroxycholanic acid, taurocholic acid, glycocholic acid, taurodesoxycholic acid, glycodesoxycholic acid, 3-hydroxy-6-ketocholanic acid and 3-hydroxy-6-ketoallocholanic acid, and the salts of bile acids are selected from the group consisting of sodium, potassium and magnesium salts of bile acids.

6. The process according to claim 4, wherein the bile acids are selected from the group consisting of monohydroxycholanic acid, dihydroxycholanic acid, trihydroxycholanic acid, taurocholic acid, glycocholic acid, taurodesoxycholic acid, glycodesoxycholic acid, 3-hydroxy-6-ketocholanic acid and 3-hydroxy-6-ketoallocholanic acid, and the salts of bile acids are selected from the group consisting of sodium, potassium and magnesium salts of bile acids.

7. The process according to claim 3, wherein the immobilized fumarase-producing microorganism is contacted with a mixture of sodium salts of taurocholic and glycocholic acids.

8. The process according to claim 4, wherein the immobilized fumarase-producing microorganism is contacted with a mixture of sodium salts of taurocholic and glycocholic acids.

9. The process according to claim 3, wherein the immobilized fumarase-producing microorganism is contacted with desoxycholic acid.

10. The process according to claim 4, wherein the immobilized fumarase-producing microorganism is contacted with desoxycholic acid.

11. The process according to claim 3, wherein the salt of fumaric acid is selected from the group consisting of sodium, potassium, ammonium, calcium, magnesium and barium fumarates.

12. The process according to claim 4, wherein the salt of fumaric acid is selected from the group consisting of sodium, potassium, ammonium, calcium, magnesium and barium fumarates.

13. The process according to claim 3, wherein the fumarase-producing microorganism is selected from the group consisting of Brevibacterium ammoniagenes IAM 1641, Brevibacterium ammoniagenes IAM 1645, Corynebacterium equi IAM 1038, Escherichia coli ATCC 11303, Microbacterium flavum IAM 1642, Proteus vulgaris IFO 3045 and Pichia farinosa IFO 0574.

14. The process according to claim 4, wherein the fumarase-producing microorganism is selected from the group consisting of Brevibacterium ammoniagenes IAM 1641, Brevibacterium ammoniagenes IAM 1645, Corynebacterium equi IAM 1038, Escherichia coil ATCC 11303, Microbacterium flavum IAM 1642, Proteus vulgaris IFO 3045 and Pichia farinosa IFO 0574.

15. The process according to claim 3, wherein the polymerization is carried out in the presence of a polymerization initiator and a polymerization accelerator at a temperature of between about 0° and 50° C.

16. The process according to claim 4, wherein the polymerization is carried out in the pressure of a polymerization initiator and a polymerization accelerator at a temperature of between about 0° and 50° C.

17. The process according to claim 3, wherein the step of contacting is carried out at a temperature of between about 0° and 50° C. and a pH of between about 5 and 10.

18. The process according to claim 4, wherein the step of contacting is carried out at a temperature of between about 0° and 50° C. and a pH of between about 5 and 10.

19. The process according to claim 3, wherein the enzymatic reaction is carried out at a temperature of between about 5° and 60° C. and a pH of between about 5 and 10.

20. The process according to claim 4, wherein the enzymatic reaction is carried out at a temperature of between about 5° and 60° C. and a pH of between about 5 and 10.

21. The process according to claim 15, wherein the polymerization initiator is selected from the group consisting of potassium persulfate, ammonium persulfate, vitamin $B_2$ and Methylene Blue, and the polymerization accelerator is selected from the group consisting of β-(dimethylamino)-propionitrile and N,N,N',N'-tetramethyl-ethylenediamine.

22. The process according to claim 16, wherein the polymerization initiator selected from the group consisting of potassium persulfate, ammonium persulfate, vitamin $B_2$ and Methylene Blue, and the polymerization accelerator is selected from the group consisting of β-(dimethylamino)-propionitrile and N,N,N',N'-tetramethyl-ethylenediamine.

23. A process for preparing L-malic acid which comprises the steps of polymerizing N,N'-lower alkylene-bis(acrylamide), bis(acrylamidomethyl)ether or N,N'-diacryl-ethyleneurea, or copolymerizing acrylamide with N,N'-lower alkylene-bis(acrylamide), bis(acrylamidomethyl)ether, N,N'-diacryl-ethyleneurea or diallylmaleate in an aqueous suspension of a fumarase-producing microorganism in the presence of a polymerization initiator and a polymerization accelerator at a temperature of between about 0° and 50° C. to produce an immobilized fumarase-producing microorganism, passing the immobilized fumarase-producing microorganism through a sieve to form granules of the immobilized fumarase-producing microorganism having a diameter of between about 0.5 and 30 mm, contacting the resultant granules with a mixture of sodium salts of taurocholic and glycocholic acids at a temperature of between about 0° and 50° C. and a pH of between about 5 and 10, and then subjecting the granules to enzymatic reaction with fumaric acid or a salt thereof at a temperature of between about 5° and 60° and a pH of between about 5 and 10.

* * * * *